(12) United States Patent
Woodard et al.

(10) Patent No.: US 11,468,985 B2
(45) Date of Patent: Oct. 11, 2022

(54) SYSTEM AND METHOD FOR MANAGING PROPERTY SHOWING APPOINTMENTS BASED ON HEALTH PARAMETERS

(71) Applicant: ShowingTime.com, Inc., Chicago, IL (US)

(72) Inventors: Scott E. Woodard, New Buffalo, MI (US); Michael P. Caputo, Aurora, IL (US)

(73) Assignee: ShowingTime.com, Inc., Costa Mesa, CA (US)

( * ) Notice: Subject to any disclaimer, the term of this patent is extended or adjusted under 35 U.S.C. 154(b) by 220 days.

(21) Appl. No.: 16/984,982

(22) Filed: Aug. 4, 2020

(65) Prior Publication Data

US 2022/0044800 A1    Feb. 10, 2022

(51) Int. Cl.
*G16H 40/67* (2018.01)
*G06Q 50/16* (2012.01)

(52) U.S. Cl.
CPC ........... *G16H 40/67* (2018.01); *G06Q 50/163* (2013.01)

(58) Field of Classification Search
CPC .............................. G16H 40/67; G06Q 50/163
See application file for complete search history.

(56) References Cited

U.S. PATENT DOCUMENTS

| | | |
|---|---|---|
| 5,014,049 A | 5/1991 | Bosley |
| 5,245,652 A | 9/1993 | Larson et al. |
| 5,280,518 A | 1/1994 | Danler et al. |
| 5,475,375 A | 12/1995 | Barrett et al. |
| 5,612,683 A | 3/1997 | Trempala et al. |
| 6,157,315 A | 12/2000 | Kokubo et al. |
| 6,385,541 B1 | 5/2002 | Blumberg |

(Continued)

FOREIGN PATENT DOCUMENTS

WO    2017174526    10/2017

OTHER PUBLICATIONS

Plowden, How to Screen for the Coronavirus at Your Property Without Breaking the Law, https://www.globest.com/2020/03/31/how-to-screen-for-the-coronavirus-at-your-property-without-breaking-the-law/?slreturn=20220420114007 (Year: 2020).*

(Continued)

*Primary Examiner* — Aryan E Weisenfeld
(74) *Attorney, Agent, or Firm* — VLP Law Group LLP; James A. D. White

(57) ABSTRACT

A real estate showing appointment management system manages showing appointments based on a health parameter of a showing contact. The health parameter can be the body temperature. The system includes a server system running a server software application and remote software application running on a remote device. The remote software application configures the thermometer of the remote device to take body temperature of the showing contact. The thermometer can be an infrared thermometer. The remote software application determines whether the body temperature meets a threshold relying on the server system or by itself. When the showing contact passes the health check, the remote software application retrieves a showing directive for the showing contact to proceed with showing the listing of a showing appointment. The showing directive is presented by the remote device for the showing contact.

16 Claims, 9 Drawing Sheets

(56) References Cited

U.S. PATENT DOCUMENTS

| | | |
|---|---|---|
| 6,496,776 B1 | 12/2002 | Blumberg |
| 6,522,875 B1 | 2/2003 | Dowling et al. |
| 6,594,633 B1 | 7/2003 | Broerman |
| 6,624,742 B1 | 9/2003 | Romano et al. |
| 6,636,803 B1 | 10/2003 | Hartz, Jr. et al. |
| 6,727,801 B1 | 4/2004 | Gervasi et al. |
| 6,842,105 B1 | 1/2005 | Henderson |
| 7,009,489 B2 | 3/2006 | Fisher |
| 7,058,395 B2 | 6/2006 | Dowling et al. |
| 7,127,475 B2 | 10/2006 | Gotz |
| 7,191,058 B2 | 3/2007 | Laird et al. |
| 7,193,503 B2 | 3/2007 | Fisher |
| 7,292,844 B2 | 11/2007 | Dowling et al. |
| 7,518,485 B2 | 4/2009 | Shuster |
| 7,606,558 B2 | 10/2009 | Despain et al. |
| 7,664,801 B2 | 2/2010 | Walker |
| 7,728,711 B2 | 6/2010 | Shoenfeld |
| 7,853,479 B2 | 12/2010 | Bengson |
| 7,869,941 B2 | 1/2011 | Coughlin |
| 7,880,584 B2 | 2/2011 | Larson et al. |
| 7,999,656 B2 | 8/2011 | Fisher |
| 8,145,352 B2 | 3/2012 | Woodard et al. |
| 8,368,507 B2 | 2/2013 | Conreux |
| 8,385,897 B1 | 2/2013 | Yadav-Ranjan |
| 8,451,088 B2 | 5/2013 | Fisher |
| 8,649,486 B1 | 2/2014 | Kellogg et al. |
| 8,754,744 B2 | 6/2014 | Woodard et al. |
| 8,831,970 B2 | 9/2014 | Weik, III |
| 8,947,530 B1 | 2/2015 | Scalisi |
| 8,971,506 B2 | 3/2015 | Kellogg et al. |
| 9,194,157 B2 | 11/2015 | Bahar |
| 9,208,466 B2 | 12/2015 | Fisher |
| 9,311,656 B2 * | 4/2016 | Barnes, Jr. ......... G06Q 10/1053 |
| 9,460,480 B2 | 10/2016 | Woodard et al. |
| 9,478,083 B2 | 10/2016 | Fisher |
| 9,514,586 B2 | 12/2016 | Rogers et al. |
| 9,536,359 B1 | 1/2017 | Gokcebay |
| 9,659,334 B2 | 5/2017 | Fenn |
| 9,659,424 B2 | 5/2017 | Huber et al. |
| 9,761,071 B2 | 9/2017 | Woodard et al. |
| 9,916,742 B2 | 3/2018 | Kuenzi |
| 9,978,192 B1 | 5/2018 | Nicosia et al. |
| 9,990,787 B2 | 6/2018 | Capaldi-Tallon |
| 10,026,248 B2 | 7/2018 | Woodard et al. |
| 10,044,519 B2 | 8/2018 | Kasmir et al. |
| 10,713,740 B1 | 7/2020 | Caputo |
| 2002/0022980 A1 | 2/2002 | Mozayeny et al. |
| 2002/0174090 A1 | 11/2002 | Dexter |
| 2003/0038708 A1 | 2/2003 | Lund |
| 2003/0154573 A1 | 8/2003 | Gould |
| 2003/0179075 A1 | 9/2003 | Greenman |
| 2005/0149432 A1 | 7/2005 | Galey |
| 2005/0168320 A1 | 8/2005 | Henderson et al. |
| 2005/0192930 A1 | 9/2005 | Hightower et al. |
| 2005/0288958 A1 | 12/2005 | Eraker et al. |
| 2006/0106628 A1 | 5/2006 | Faherty et al. |
| 2006/0220809 A1 | 10/2006 | Stigall et al. |
| 2007/0100644 A1 | 5/2007 | Keillor et al. |
| 2007/0143173 A1 | 6/2007 | Walker |
| 2007/0266081 A1 | 11/2007 | Murchison |
| 2007/0290798 A1 | 12/2007 | Larson et al. |
| 2008/0168369 A1 | 7/2008 | Tadman |
| 2008/0169937 A1 | 7/2008 | Lowry |
| 2011/0053557 A1 | 3/2011 | Despain et al. |
| 2012/0290203 A1 | 11/2012 | King |
| 2013/0005368 A1 | 1/2013 | Hunziker |
| 2013/0262186 A1 | 10/2013 | Lazarre |
| 2013/0282524 A1 | 10/2013 | Appolito et al. |
| 2014/0258042 A1 | 9/2014 | Butler |
| 2014/0304178 A1 | 10/2014 | Bengson |
| 2015/0077220 A1 | 3/2015 | Davis |
| 2015/0235145 A1 | 8/2015 | Dubuc |
| 2016/0180620 A1 | 6/2016 | Eyring et al. |
| 2016/0241999 A1 | 8/2016 | Chin et al. |
| 2018/0075681 A1 | 3/2018 | Scalisi et al. |
| 2018/0232978 A1 | 8/2018 | Schmidt-Lackner |
| 2019/0244455 A1 | 8/2019 | Kim et al. |
| 2019/0327448 A1 | 10/2019 | Fu et al. |

OTHER PUBLICATIONS

Huawei's temperature-taking smartphone is the most 2020 phone of 2020, Ron Amadeo, Jun. 4, 2020, https://arstechnica.com.

Huwaei announces a phone that can take your temperature, Jules Wang, Jun. 3, 2020, https://www.androidpolice.com.

Huawei's clever new smartphone can take your temperature, Jun. 8, 2020, https://www.fastcompany.com.

Developing an infrared thermometer with an app based on the wifi modules of Alios, Apr. 17, 2020, https://www.alibabacloud.com.

The Hottest thermometer. The coolest technology., https://www.withings.com/us/en/thermo.

Bluetooth Thermometers, https://www.medicalexpo.com/medical-manufacturer/bluetooth-thermometer-44144.html.

* cited by examiner

SYSTEM AND METHOD FOR MANAGING PROPERTY SHOWING APPOINTMENTS BASED ON HEALTH PARAMETERS

CROSS-REFERENCE TO RELATED APPLICATIONS

NONE.

FIELD OF THE DISCLOSURE

The present invention relates generally to systems and methods for managing real estate property showing appointments, and more particularly relates to a system and method that manages real estate property showing appointments based on a health parameter. More particularly still, the present disclosure relates to a system and method that manages real estate property showing appointments based on the body temperature of a showing contact.

DESCRIPTION OF BACKGROUND

A real estate property showing appointment management system allows users (such as listing agents, showing agents, sellers, buyers, tenants, and others) to manage listings, listing agent profiles, showing agent profiles and showings of the listings. The real estate property showing appointment management system also allows users to schedule showing appointments, create the showing appointments, manage the showing appointments, communicate with others regarding real estate listings, collect and forward showing feedback, etc. A showing appointment indicates the listing, the time or time period of the showing and the showing agent. Listing agents access the real estate property showing appointment management system to configure their listings of real estate properties in the real estate property showing appointment management system. A listing includes descriptions of the underlying real estate property, contact information of listing contacts (such as the listing agent, the listing office, the seller, etc.), showing instructions of the listing for showing agents, available showing time of the listing, etc.

Showing agents access the real estate property showing appointment management system to make showing appointments for showing real estate properties to their clients, such as prospect home buyers and tenants. As used herein, the showing agents, the prospect home buyers, the prospect tenants and other types of individuals on the showing side are referred to herein as showing contacts. The real estate property showing appointment management system also manages communications between the listing contacts and the showing contacts. For instance, when a showing agent schedules a showing appointment, the system communicates with the listing agent to confirm the showing appointment. As another example, the system manages requests for showing feedback from showing agents; receives feedback from showing agents; and forwards feedback to listing agents. The system is accessible via mobile apps and showing software applications running on desktop, laptop and/or tablet computers over the Internet.

At the time of a particular showing appointment, the showing agent visits the listing and shows the underlying real estate property to her/his client. To do so, the showing agent uses a mobile app running on a mobile device (such as a smartphone) and communicating with the server system of the real estate property showing appointment management system over the Internet. The mobile app retrieves a showing pass, showing instructions and/or the listing access details from the showing appointment management system over the Internet. The showing pass is set forth in U.S. Pat. No. 10,713,740.

However, showing real estate properties during a pandemic, such as the COVID-19 pandemic of 2020, raises concerns for the listings' owners, residents and other related persons. For instance, a home owner and/or the corresponding listing agent may not like or prohibit any person with a contagious virus to visit her/his property. The infected persons usually have body temperatures above the normal level. Accordingly, there is a need for an improved real estate property showing appointment management system that limits showing of listings when a showing contact exhibits a symptom of a virus. Furthermore, there is a need for an improved real estate property showing appointment management system that limits showing of listings when a showing contact exhibits an abnormal body temperature.

SUMMARY OF THE DISCLOSURE

Generally speaking, pursuant to the various embodiments, the present disclosure provides an improved real estate showing appointment management system based on a set of health parameters. The system includes a database storing and providing real estate showing appointment data; a real estate showing appointment management server system having a server processing unit, a memory, and a network interface operatively coupled to the processing unit and operatively coupled to the database and the Internet; a specialized server software application running on the server processing unit; and a specialized remote software application running on a remote electronic communication device adapted to communicate with the real estate showing appointment management server system over the Internet. The specialized remote software application is adapted to request a set of showing appointments from the specialized server software application over the Internet; receive the set of showing appointments from the specialized server software application over the Internet; present the set of showing appointments on a display screen of the remote electronic communication device; in response to an input, select a showing appointment from the set of showing appointments, thereby forming a selected showing appointment; determine a first geographical location of a listing corresponding to the selected showing appointment; determine a second geographical location of the remote electronic communication device; determine whether the remote electronic communication device is within a geofence of the listing based on the geofence, the first geographical location and the second geographical location; and, when the remote electronic communication device has moved into the geofence, perform a health check process for determining whether a set of showing contacts should be allowed to proceed with the selected showing appointment. The health check process includes configuring the remote electronic communication device to determine a set of values of a health parameter for the set of showing contacts respectively; retrieving the set of values from the remote electronic communication device; and determining whether the set of values matches a set of health thresholds by itself or relying the specialized server software application. The specialized remote software application is further adapted to, when the set of values matches the set of health thresholds, retrieve a showing directive for the selected showing appointment from the specialized server software application; and present showing directive via the remote electronic communication device. The showing directive is displayed on the display screen of the remote electronic communication device, or presented in an audio format. The health parameter is a human body temperature parameter. The set of values is determined by a thermometer. The set of health thresholds includes a normal body temperature limit. The set of values matches a set of health thresholds when each value within the set of values is below the normal body temperature limit. The set of values does not match the set of health thresholds when any value within the set of values is above the normal body temperature limit. The thermometer is an infrared thermometer. The showing directive includes at least one of a showing pass or a key code corresponding to the selected showing appointment. The showing directive further includes a set of showing instructions. The health check process further includes presenting a set of health inquiries via the remote electronic communication device; retrieving a set of responses to the set of health inquiries via the remote electronic communication device; and determining whether the set of responses meets a set of health requirements by itself or relying on the specialized server software application.

Further in accordance with the present teachings is a method for managing showing appointment based on a set of health parameters. The method is performed by a real estate showing appointment management system. It includes receiving a request for making a showing appointment of a listing; creating the appointment; requesting a listing contact of the listing to confirm the showing appointment; receiving a confirmation of the showing appointment; indicating the showing appointment as confirmed; presenting the showing appointment on a display screen of a remote electronic communication device; determining a first geographical location of the listing; determining a second geographical location of the remote electronic communication device; determining whether the remote electronic communication device is within a geofence of the listing based on the geofence, the first geographical location and the second geographical location; and, when the remote electronic communication device has moved into the geofence, performing a health check process to determine whether a set of showing contacts should be allowed to proceed with the showing appointment. The health check process includes configuring the remote electronic communication device to determine a set of values of a health parameter for the set of showing contacts respectively; retrieving the set of values from the remote electronic communication device; and determining whether the set of values matches a set of health thresholds. The method further includes, when the set of values matches the set of health thresholds, presenting a showing directive via the remote electronic communication device. The showing directive is displayed on the display screen of the remote electronic communication device; or presented in an audio format. The health parameter is a human body temperature parameter. The set of values is determined by a thermometer. The set of health thresholds includes a normal body temperature limit. The set of values matches a set of health thresholds when each value within the set of values is below the normal body temperature limit. The set of values does not match the set of health thresholds when any value within the set of values is above the normal body temperature limit. The thermometer is an infrared thermometer. The showing directive includes at least one of a showing pass or a key code corresponding to the selected showing appointment. The showing directive further includes a set of showing instructions. The health check process further includes presenting a set of health inquiries via the remote electronic communication device; retrieving a set of responses to the set of health inquiries via the remote electronic communication device; and determining whether the set of responses meets a set of health requirements.

BRIEF DESCRIPTION OF THE DRAWINGS

Although the characteristic features of this disclosure will be particularly pointed out in the claims, the invention itself, and the manner in which it may be made and used, may be better understood by referring to the following description taken in connection with the accompanying drawings forming a part hereof, wherein like reference numerals refer to like parts throughout the several views and in which:

A person of ordinary skills in the art will appreciate that elements of the figures above are illustrated for simplicity and clarity, and are not necessarily drawn to scale. The dimensions of some elements in the figures may have been exaggerated relative to other elements to help understanding of the present teachings. Furthermore, a particular order in which certain elements, parts, components, modules, steps, actions, events and/or processes are described or illustrated may not be actually required. A person of ordinary skills in the art will appreciate that, for the purpose of simplicity and clarity of illustration, some commonly known and well-understood elements that are useful and/or necessary in a commercially feasible embodiment may not be depicted in order to provide a clear view of various embodiments in accordance with the present teachings.

DETAILED DESCRIPTION

Figure 1:
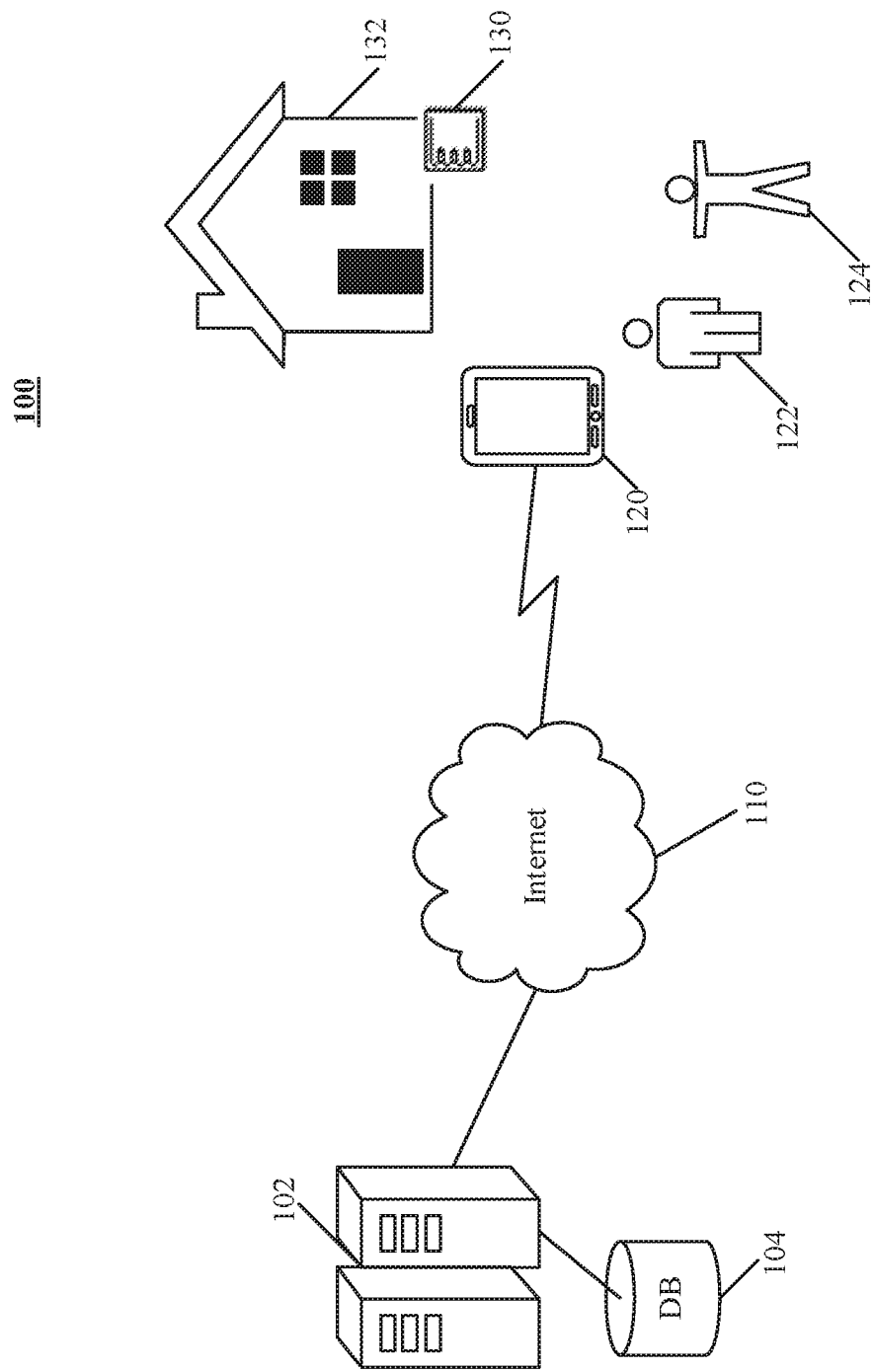
FIG. 1 is an illustrative block diagram of a real estate showing system in accordance with the teachings of this disclosure.

Turning to the Figures and to FIG. 1 in particular, a real estate showing system in accordance with the present teachings is shown and generally indicated at 100. The real estate showing system 100 is adapted to perform processes in accordance with the present teachings to manage showing appointments based on one or more health parameters of showing contacts. In one illustrative embodiment, the real estate showing system 100 includes a real estate showing appointment management server system 102, which comprises one or more servers (such as a cloud server system, a server farm or a set of individual servers), and one or more databases 104 for storing listing contacts, listings, showing appointments, showing media, showing data, etc. The databases 104 (such as a cloud database system, a relational database system, an in-memory database, etc.) are operatively coupled to the servers 102 via, for example, networking links.

The real estate showing system 100 further includes remote electronic communication devices, one of which is illustrated and indicated at 120, communicating with the server system 102 via the Internet 110. The remote device 120 can be a smartphone, a tablet computer (such as an iPad™), a laptop computer or other types of mobile devices. The remote devices are operated by showing contacts, such as a showing agent 122.

The server system 102 runs a specialized server software application for managing listings, scheduling showings and managing showing appointments. The specialized server software application is physically loaded in a single server or distributed across multiple servers within the server system 102. The specialized server software application includes one or more computer software programs coded using computer programming languages, such as Java, C#, etc. Moreover, the showing management system 102 integrates with or connects to one or more listing services (not shown) to update the database 104 of real estate property listings and other real estate related data.

Figure 2:
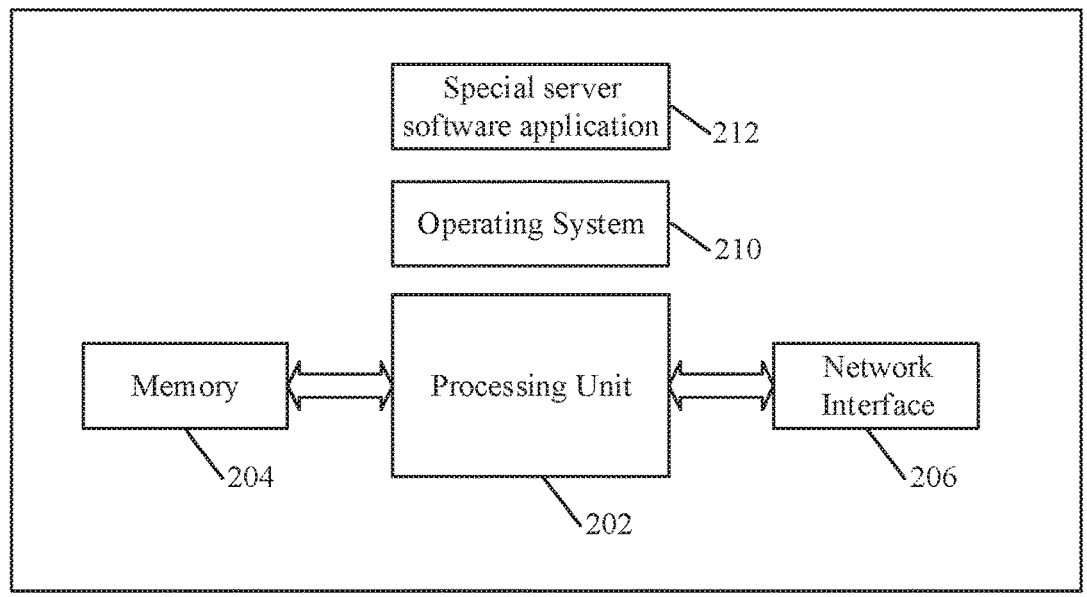
FIG. 2 is an illustrative block diagram of a real estate showing appointment management server system in accordance with the teachings of this disclosure.

In accordance with the present teachings, as shown in FIG. 2, each server 102 includes a server processing unit 202, one or more server network interfaces 206 through which the server system 102 accesses the Internet 102 and communicates with the database 104, and some amount of server memory 204. The network interface 206 and the memory 204 are operatively coupled to the processing unit 202. An operating system (such as Windows and Linux) 210 runs on the processing unit 202. The server system 102 further includes the special server software application indicated at 212 executed by the processing unit 202 for managing listings, and showing appointments.

Each of the remote electronic communication devices 120 includes a processing unit, an audio output interface (such as a speaker), an audio input interface (such as a microphone), a user input interface (such as a touch screen), some amount of memory, a video output interface (such as a display screen), a video input interface (such as a camera), and a network interface. The elements of the remote device 120 are operatively coupled to its processing unit. The remote electronic communication device 120 further includes a special remote computer software application executed by its processing unit. The special remote computer software application includes one or more computer software programs coded using computer programming languages, and is also referred to herein as a mobile app.

The showing agent 122 operates the remote device 120 and visits the real estate property 132 for showing the same for her/his client 124, The client 124 can be, for example, a prospect buyer, a prospect tenant, or a professional for accessing the property 132. The property 132 is represented as a listing inside the showing system 102. The special remote computer software application running on the remote device 120 communicates with the server system 102 for managing the showing, To gain physical access to the listing 132, the showing agent 122 operates a listing physical access control device 130. The device 130 can be, for example, a lockbox 130. The access control device 130 allows or disallows the showing agent 122 to get into the listing 132.

Figure 3:
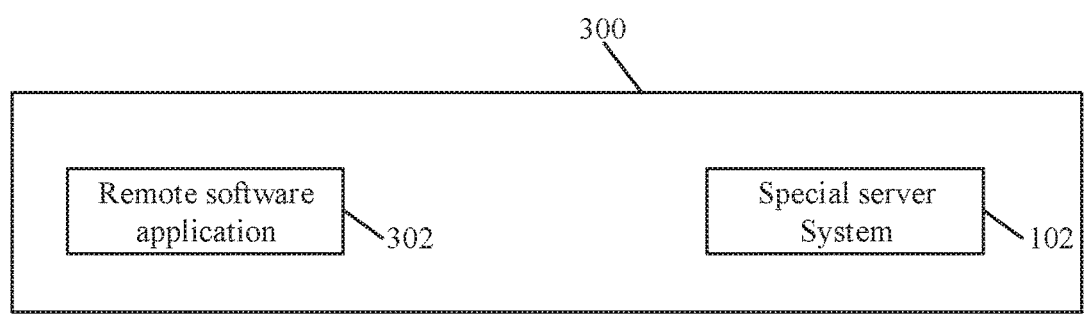
FIG. 3 is an illustrative block diagram of a real estate showing appointment management system in accordance with the teachings of this disclosure.
Figure 4:
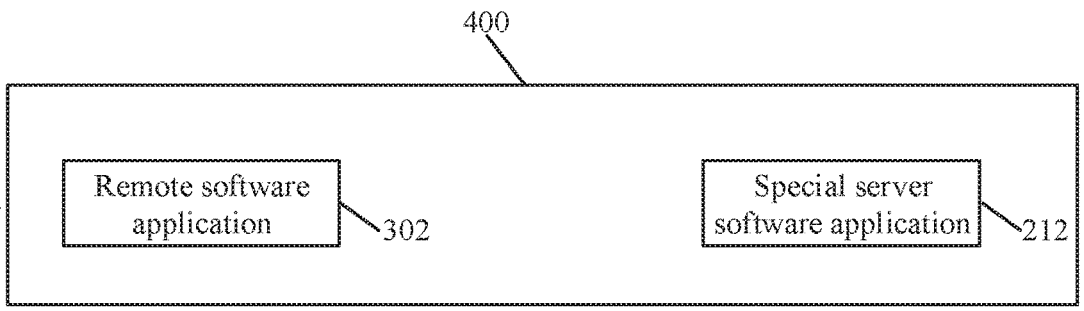
FIG. 4 is an illustrative block diagram of a real estate showing appointment management software system in accordance with the teachings of this disclosure.

Referring to FIGS. 3 and 4, the special remote computer software application is indicated at 302. The server system 102 with the specialized server software application 212 and the remote software application 302 are collectively referred to herein as the real estate showing appointment management system, indicated at 300. The specialized server software application 212 and the remote software application 302 are collectively referred to herein as the real estate showing appointment management software system, indicated at 400. The real estate showing appointment management software system 400 is a subsystem of the real estate showing appointment management system 300.

The real estate showing agent 122 operates a computer, such as the remote device 120 or a desktop computer, to access the showing appointment management system 300 to schedule showing appointments for showing real estate properties (also referred to herein as listings), provide showing feedback, and retrieve showing appointments. The showing appointment can be encoded into a showing pass, such as a machine readable optical label or barcode. A listing contact (such as a listing agent and the seller of a listing) can also use a computer to access the showing appointment management system 300 to manage listings, confirm showing appointments, and retrieve showing feedback. Such features can also be performed by mobile devices, such as a smartphones and tablet computers.

Figure 5:
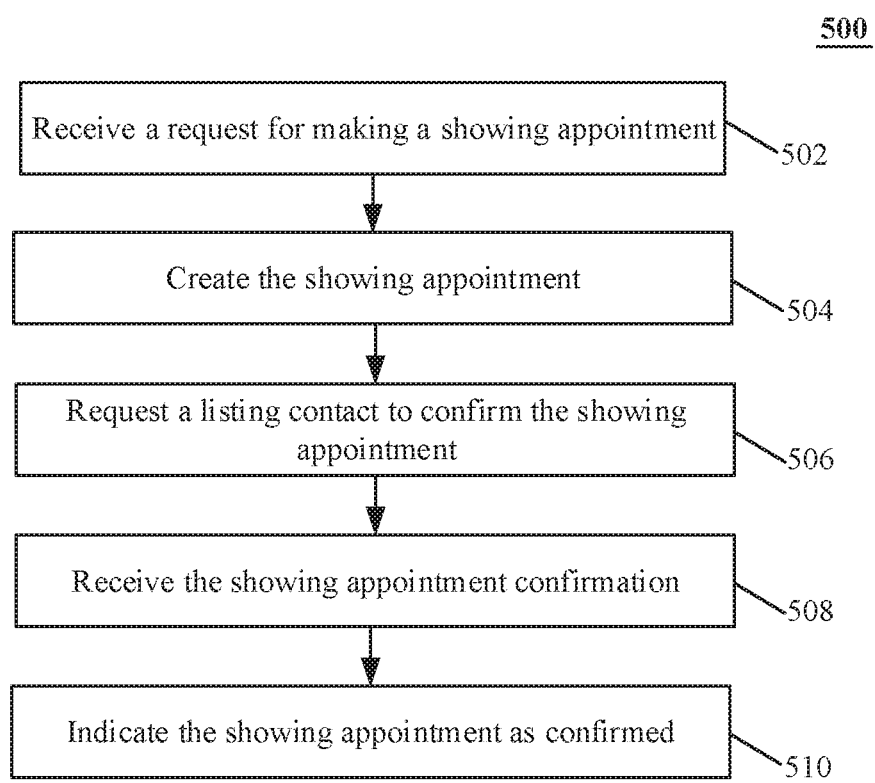
FIG. 5 is a flowchart illustrating a process by which a real estate showing appointment management system creates showing appointments in accordance with the teachings of this disclosure.

Referring now to FIG. 5, a flowchart depicting a process by which the showing appointment management system 300 creates showing appointments is shown and generally indicated at 500. At 502, the server software application 212 receives a request for making a showing appointment to show a particular listing, such as the listing 132, The showing appointment request can be made by the showing agent 120 through the remote device 122 or a different computer. At 504, the server software application 212 creates the showing appointment, and stores it into the database 104. At 506, the server software application 212 sends a request to a listing contact (such as the listing agent) to confirm the showing appointment. Once the listing contact confirms the showing appointment, at 508, the server software application 212 receives the confirmation. At 510, the server software application 212 indicates that the showing appointment has been confirmed. The indication can be done by modifying database records stored in the database 104. At this point, the showing appointment has been successfully scheduled.

Figure 6A:
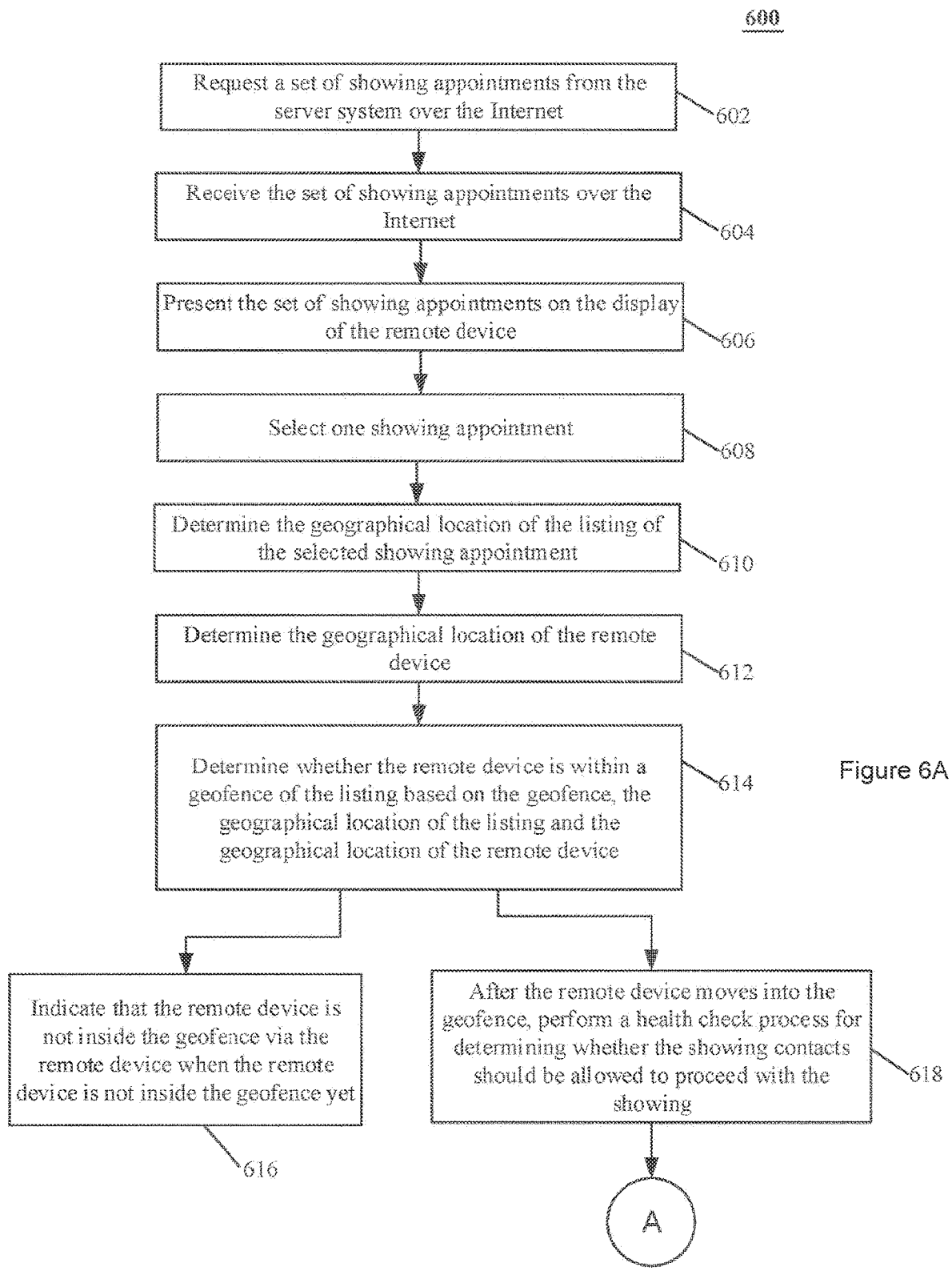
FIGS. 6A and 6B are a flowchart illustrating a process by which a real estate showing appointment management system manages showing appointments based on a set of health parameters in accordance with the teachings of this disclosure.
Figure 6B:
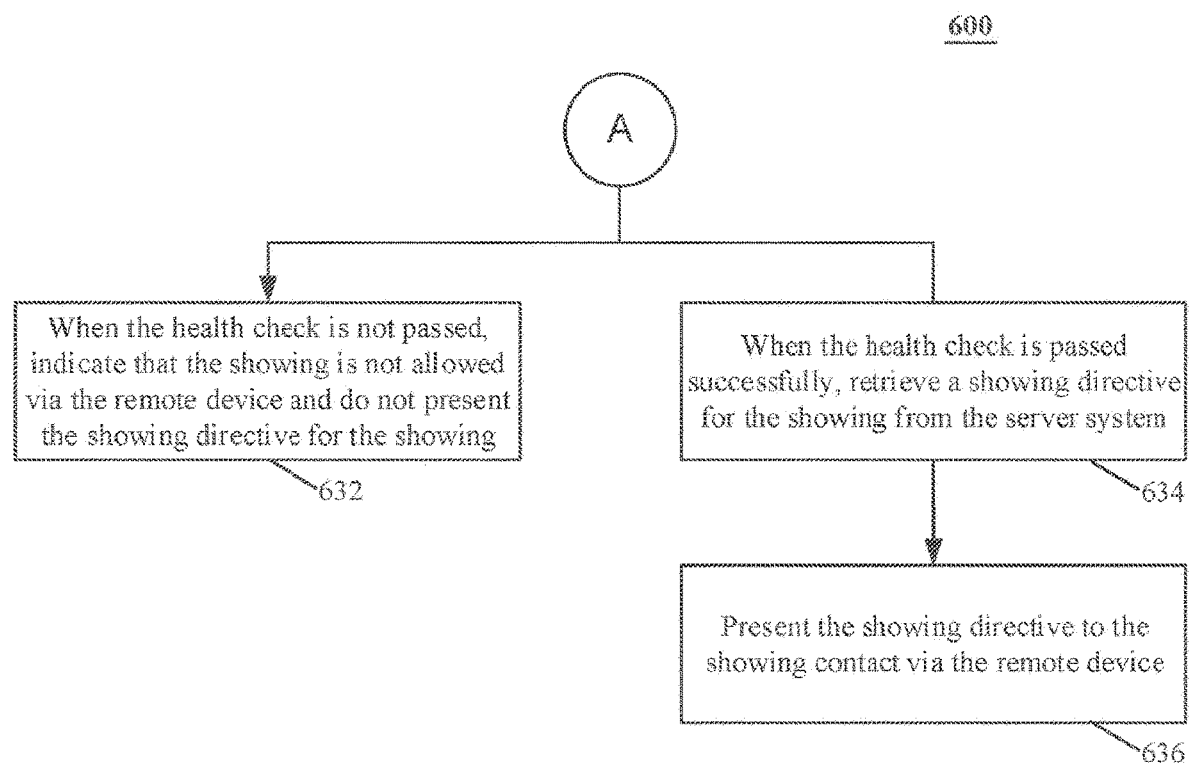

Referring now to FIGS. 6A and 6B, a flowchart depicting a process by which the showing appointment management system 300 manages showing appointments based on health parameters is shown and generally indicated at 600. At 602, the special remote computer software application 302 sends to the special server software application 212 a request for showing appointments of the showing agent 122 over the Internet 110. For example, when the remote software application 302 requests all showing appointments of the showing agent 122 of a particular day, within a particular amount of time from the current time, within a particular range of the current geographical location (i.e., GPS location) of the remote device 120, etc. Taking the particular day scenario as an example, the remote software application 302 may request all showing appointments of the showing agent 122 for the current day. As another example, the remote software application 302 sends the current GPS location of the remote device 120 to the server software application 212, and indicates a request for showing appointments of listings within a predetermined radius of the GPS location.

In response, the server software application 212 retrieves the set of showing appointments meeting the criteria of the request from the database 104, and sends the same to the remote device 120. At 604, the remote software application 302 receives the set of showing appointments. At 606, the remote software application 302 presents the set of showing appointments and/or the underlying listings on a display screen of the remote device 120. The showing agent 122 selects one of them via the input interface of the remote device 120. In response to the showing agent's 122 selection input, at 608, the remote software application 302 selects one showing appointment from the set. At 610, the remote software application 302 determines the geographical location of the listing of the selected showing appointment. In one implementation, the geographical location is provided as part of the showing appointment data received at 604. In a different implementation, it is requested from the server software application 212. For instance, it is part of the listing data of the listing that is provided to the remote software application 302 separate from the showing appointment data. In yet another different implementation, the geographical location is not provided to the remote device 120. In such a case, at 610, the remote software application 302 determines that the geographical location is only available to the server software application 212.

At 612, the remote software application 302 determines the geographical location (i.e., GPS location) of the remote device 120. The element 612 may be performed periodically. At 614, based on a geofence of the listing 132 and the GPS locations of the listing 132 and the remote device 120, the remote software application 302 determines whether the remote device 120 is within the geofence of the listing 132. The geofence defines a range around the listing 132. The range can be defined by a radius, such as fifty meters, or a rectangular or square area around the listing 132. In one implementation, the geofence is provided as part of the showing appointment data received at 604. In a different implementation, it is requested from the server software application 212. For instance, it is part of the listing data of the listing 132 that is provided to the remote software application 302 separate from the showing appointment data received at 604.

As used herein, the GPS location of the remote device 120 is deemed to be that of the showing agent 122. When the remote device 120 is not inside the geofence, at 616, the remote software application 302 indicates that the showing agent 122 is not at the listing 132 yet. The indication can be, for example, a message displayed on the screen of, a video message played by, or an audio message played back by the remote device 120.

When the remote device 120 moves into the geofence, the remote software application 302 interprets that the showing agent 122 is at the listing 132 now. In such a case, at 618, the remote software application 302 performs a health check on the showing contacts 122-124 to determine whether they should be allowed to proceed with the showing. If allowed, the showing agent 122 can then proceed with the showing appointment, access the listing 132 and show it to the prospect buyer 124. When showing contacts 122-124 fail the health check (meaning that the health check is not passed), at 632, the remote software application 302 indicates that the showing contacts 122-124 are not allowed to access the listing 132 since one of them has failed the heath check. The indication can be, for example, a message displayed on the screen of, a video message played by, or an audio message played back by the remote device 120.

When the showing contacts 122-124 fail the health check (meaning that the health check is not passed), at 632, the remote software application 302 indicates that the showing contacts 122-124 are not allowed to access the listing 132 since one of them has failed the heath check. The indication can be, for example, a message displayed on the screen of, a video message played by, or an audio message played back by the remote device 120. When the showing contacts 122-124 pass the health check (meaning that the health check is passed), at 634, the remote software application 302 retrieves a showing directive for the selected showing appointment. The showing directive allows the showing agent 122 to move forward with the showing of the listing 132. Without the showing directive, the showing contact 122 cannot proceed with the showing.

In one implementation, the showing directive is provided at 604 as part of the showing appointment data. Alternatively, the showing directive is separately requested from the server software application 212 by the remote software application 302. The showing directive can be a showing pass. The showing pass is scanned by the listing access control device 130. Once the listing access control device 130 verifies the showing pass directly or indirectly, the listing 132 is opened for access by the showing agent 122 to show it for the prospect buyer 124. The showing directive can also be a different type of access credentials, such as a key code, to open the listing access control device 130. It is displayed on the screen of or played back as an audio message by the remote device 120. Moreover, the showing directive can include one or more showing instructions. The showing instructions are configured by the listing agent and/or the owner of the property 132. They direct the showing contacts 122-124 to do and/or not to do certain things during the showing of the house 132.

Figure 7:
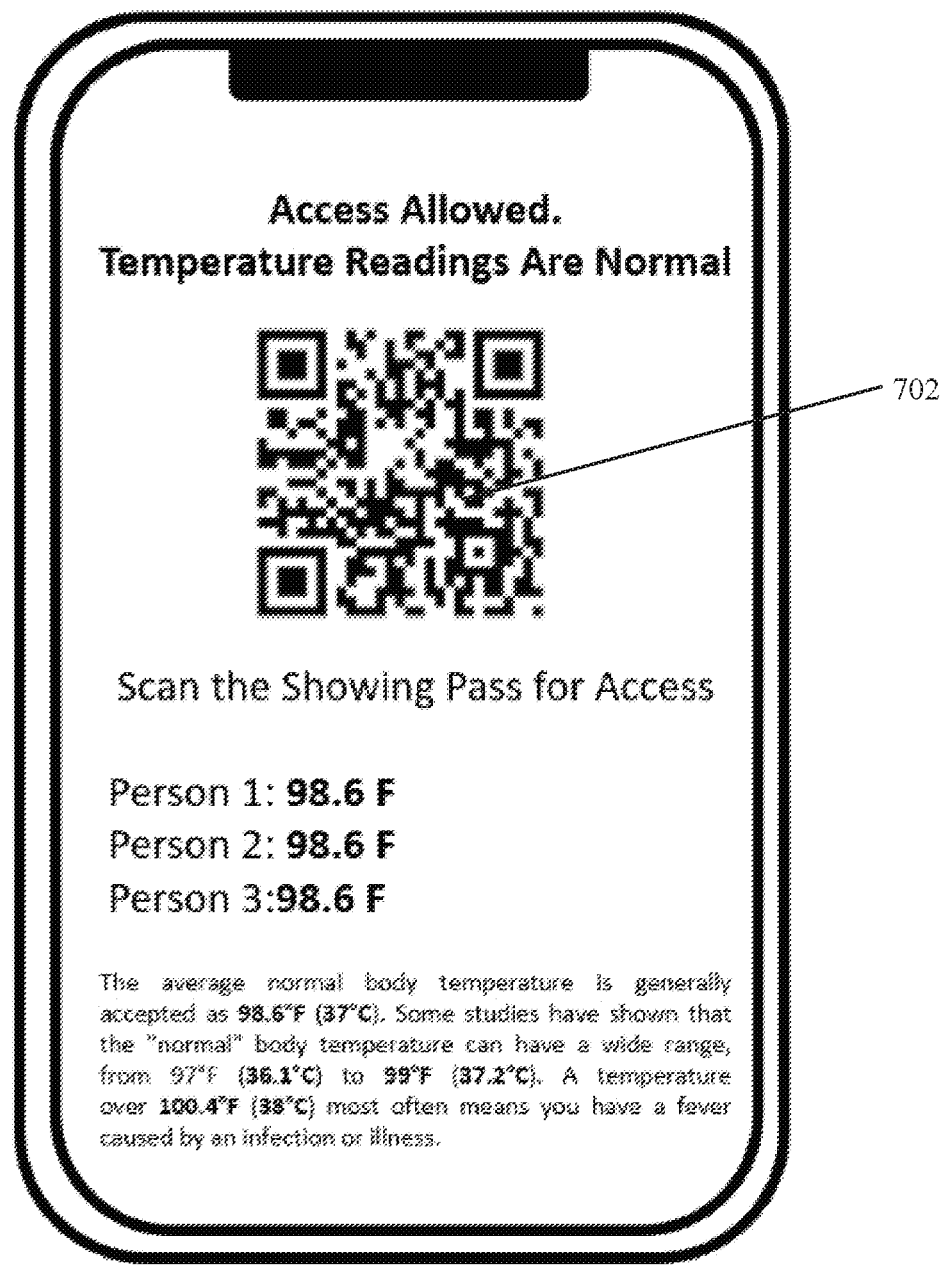
FIG. 7 is an illustrative screenshot of a remote electronic communication device showing a showing directive in accordance with the teachings of this disclosure.

At 636, the remote software application 302 presents the showing directive to the showing agent 122 by the remote device 120. An illustrative showing directive is shown in FIG. 7. Referring to FIG. 7, an illustrative screenshot of the remote device 120 showing a showing directive 702 is shown and generally indicated at 700. The illustrative showing directive 702 is a showing pass.

Figure 8:
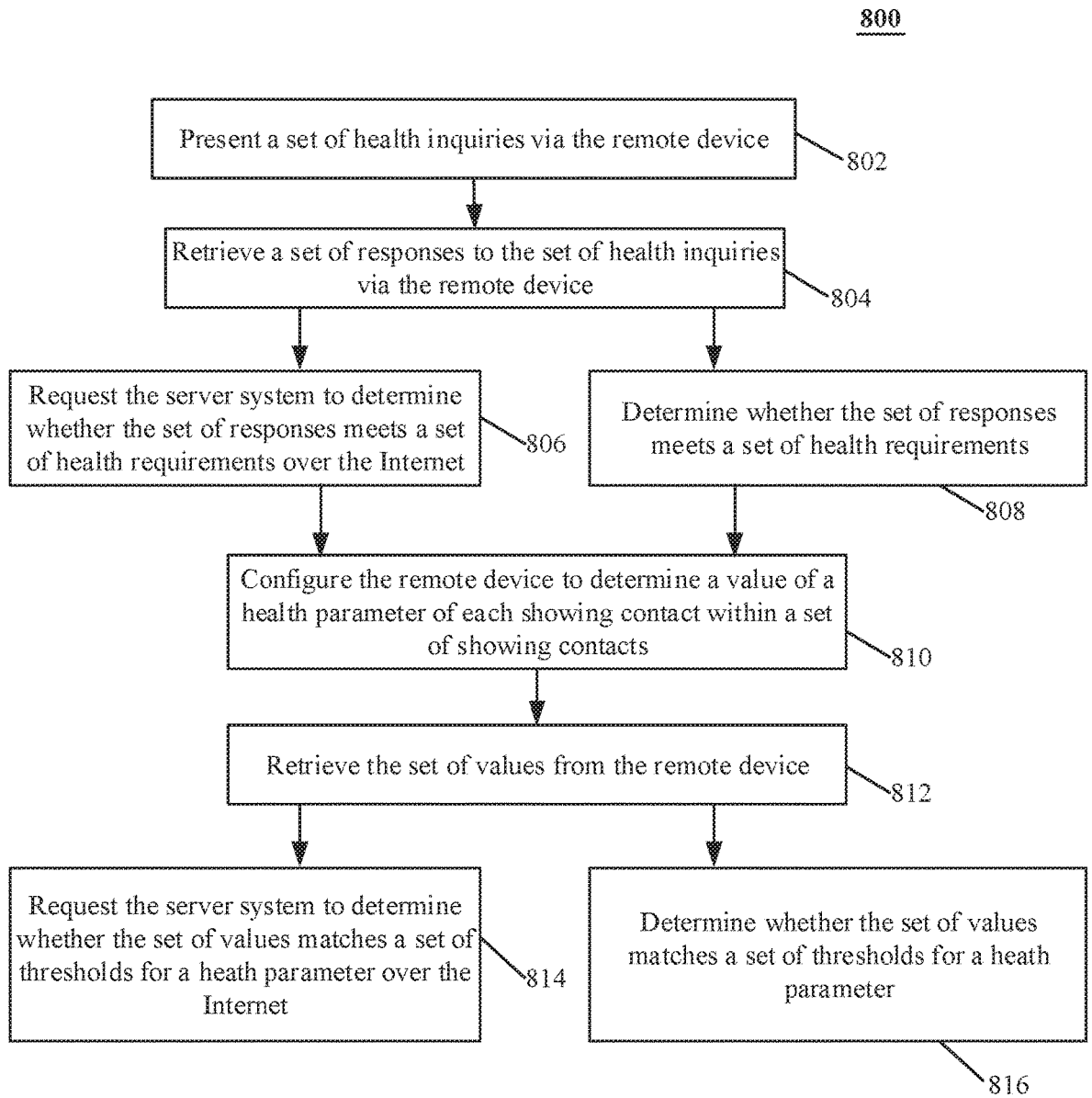
FIG. 8 is a flowchart illustrating a process by which a remote computer software application performs a health check on a set of showing contacts in accordance with the teachings of this disclosure.

The health checking process performed at 618 is further illustrated by reference to FIGS. 8, 9 and 10. Turning first to FIG. 8, a flowchart illustrating a process by which the remote computer software application 302 performs to check a set of health parameters of the showing contacts 122-124 is shown and generally indicated at 800. At 802, the remote software application 302 presents a set of health inquiries via the remote device 120. The presentation may take the form of audio, text, graphical and/or video. An illustrative presentation of the health inquiries is shown in FIG. 9.

Figure 9:
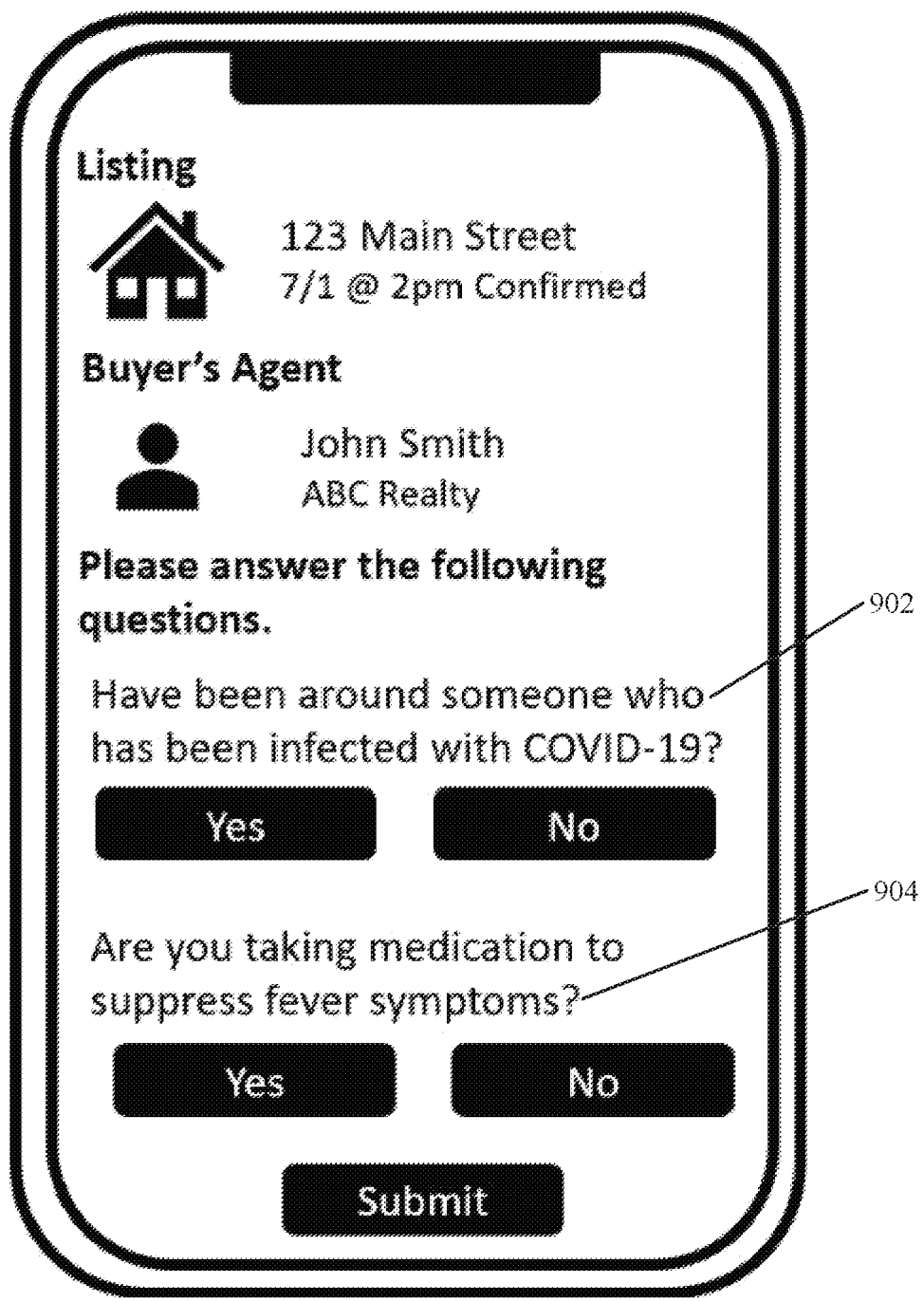
FIG. 9 is an illustrative screenshot of a set of health inquiries for a real estate showing appointment presented by a remote computer software application on a remote electronic communication device in accordance with the teachings of this disclosure.

Referring to FIG. 9 now, an illustrative screenshot of the set of health inquiries 902 and 904 is shown and generally indicated at 900. Via the screen 900, the showing agent 122 enters her/his responses, and then submits the responses.

Turning back to FIG. 8, at 804, the remote software application 302 retrieves the responses entered by the showing agent 122. In one implementation, at 806, the remote software application 302 submits the set of responses to the server software application 212 and requests it to determine whether the set of responses meets a set of health requirements. For example, for the showing agent 122 to proceed with the showing, the response to the inquiry 902 needs to be No. The remote software application 302 is said to determine whether the set of responses meets the set of health requirements relying on the server software application 212.

Alternatively, the server software application 212 provides the set of health requirements to the remote software application 302, In such a case, at 808, the remote software application 302 compares the set of responses to the set of health requirements to determine whether the set of responses meets the set of health requirements. In such a case, remote software application 302 is said to determine whether the set of responses meets the set of health requirements by itself.

At 810, the remote software application 302 configures the remote device 120 to determine the value of a health parameter of each showing contact within the set of showing contacts 122-124. In one embodiment, the health parameter is the human body temperature. The remote electronic device 120, such as a smartphone, is capable of obtaining the body temperature of the showing agents 122-124. For instance, the remote device 120 is capable to detect the human body temperature by incorporating an infrared thermometer. At 810, the remote software application 302 activates and/or accesses the infrared thermometer via, for example, an application programming interface ("API") call. In one implementation, right before or after the element 808, the remote software application 302 instructs the showing agent 122 to take certain steps, such as placing the top-rear end of the remote device 120 against or near her/his forehead for taking her/his body temperature. The instruction may also include what actions, such as pressing a button, the showing agent 122 should take for taking her/his body temperature. More than one health parameter can be operated on at 810.

At 812, the remote software application 302 retrieves the body temperature of the showing contact. For instance, the temperature is returned via a call back to the remote software application 302, or another API call to request the temperature. The body temperature retrieved at 812 is a value of the body temperature health parameter. The body temperature is taken of each showing contact. At 814, the remote software application 302 submits the set of values to the server system 102, and requests the server software application 212 to determine whether the set of values matches a set of thresholds. For instance, with the normal human body temperature range being 97°-99°, the threshold can be 99°. If any value within the set is above 99°, it is said herein that the set of values does not match the threshold and the showing contacts 122-124 have failed the health check. On the other side, if all values within the set are not above 99°, it is said that the set of values does match the threshold and the showing contacts 122-124 have passed the health check. When the remote software application 302 requests the server software application 212 to determine whether the set of values matches a set of thresholds, it is also said that the remote software application 302 determines whether the set of values matches a set of thresholds relying on the server software application 212.

In a different implementation, at 816, the remote software application 302 determines whether the set of values matches a set of thresholds. In such a case, the remote software application 302 retrieves the set of health thresholds from the server software application 302. The set of health thresholds can be retrieved at 604. Alternatively, it is retrieved via a separate request to the server system 102.

After 814 and 816, the remote software application 302 performs the element 634. In such a case, it is said that the remote software application 302 determines whether the set of values matches a set of thresholds by itself.

Figure 10:
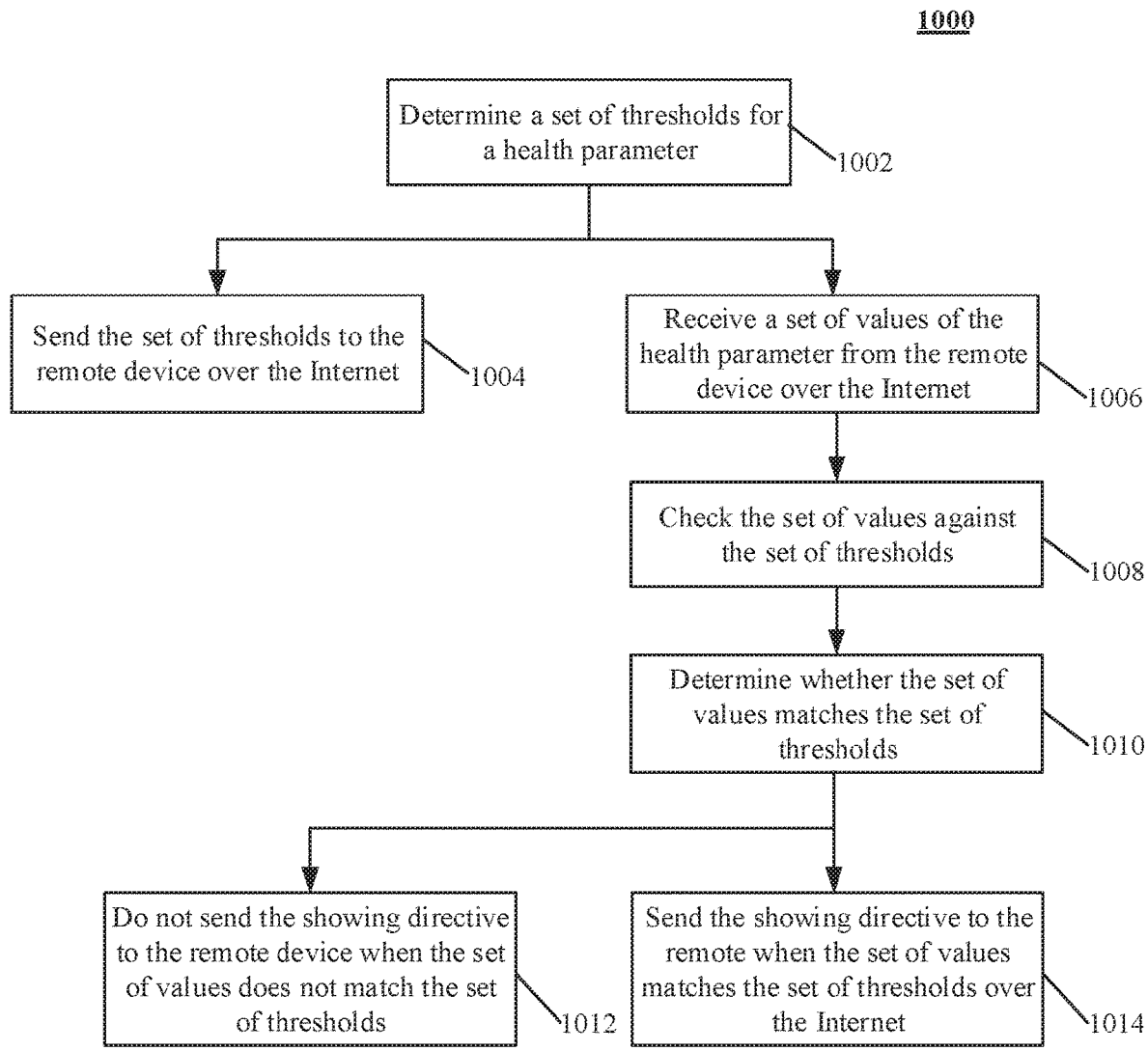
FIG. 10 is a flowchart illustrating a process by which a special real estate showing appointment management server software application manages showing appointments based on a health parameter in accordance with the teachings of this disclosure.

Referring to FIG. 10, a flowchart depicting a process by which the special server software application 212 manages showing appointments based on a health parameter is shown and generally indicated at 1000. At 1002, the server software application 212 determines the set of thresholds for a health parameter, such as that referenced at 800. The set of thresholds can be enabled and/or configured by the listing agents, home owners, the provider of the system 300, etc., and stored in the database 104. At 1004, the server software application 212 sends the set of thresholds to the remote software application 302. For instance, it is sent along with the showing appointment data. Alternatively, it is sent in response to a request from the remote software application 302.

Alternatively, the server software application 212 does not send the set of health thresholds to the remote device 120. In such a case, at 1006, the server software application 212 receives the set of values sent at 814. At 1008, the server software application 212 compares the set of values against the set of thresholds. At 1010, the server software application 212 determines whether the set of values matches the set of thresholds. When the set of values does not match the set of thresholds, at 1012, the server software application 212 does not send the showing directive to the remote device 120, such that the showing agent 122 cannot proceed with the showing of the listing 132. On the other side, when the set of values does match the set of thresholds, at 1014, the server software application 212 sends the showing directive to the remote device 120, such that the showing agent 122 can proceed with the showing of the listing 132.

Obviously, many additional modifications and variations of the present disclosure are possible in light of the above teachings. Thus, it is to be understood that, within the scope of the appended claims, the disclosure may be practiced otherwise than is specifically described above.

The foregoing description of the disclosure has been presented for purposes of illustration and description, and is not intended to be exhaustive or to limit the disclosure to the precise form disclosed. The description was selected to best explain the principles of the present teachings and practical application of these principles to enable others skilled in the art to best utilize the disclosure in various embodiments and various modifications as are suited to the particular use contemplated. It is intended that the scope of the disclosure not be limited by the specification, but be defined by the claims set forth below. In addition, although narrow claims may be presented below, it should be recognized that the scope of this invention is much broader than presented by the claim(s). It is intended that broader claims will be submitted in one or more applications that claim the benefit of priority from this application. Insofar as the description above and the accompanying drawings disclose additional subject matter that is not within the scope of the claim or claims below, the additional inventions are not dedicated to the public and the right to file one or more applications to claim such additional inventions is reserved.

What is claimed is:

1. A real estate showing appointment management system for managing showing appointment based on a set of health parameters, said real estate showing appointment management system comprising:

i) a database storing and providing real estate showing appointment data;

ii) a real estate showing appointment management server system having a server processing unit, a memory, and a network interface operatively coupled to said processing unit and operatively coupled to said database and the Internet;
iii) a specialized server software application running on said server processing unit;
iv) a specialized remote software application running on a remote electronic communication device adapted to communicate with said real estate showing appointment management server system over the Internet;
v) said specialized remote software application adapted to:
1) request a set of showing appointments from said specialized server software application over the Internet;
2) receive said set of showing appointments from said specialized server software application over the Internet;
3) present said set of showing appointments on a display screen of said remote electronic communication device;
4) in response to an input, select a showing appointment from said set of showing appointments, thereby forming a selected showing appointment;
5) determine a first geographical location of a listing corresponding to said selected showing appointment;
6) determine a second geographical location of said remote electronic communication device;
7) determine whether said remote electronic communication device is within a geofence of said listing based on said geofence, said first geographical location and said second geographical location;
8) when said remote electronic communication device has moved into said geofence, perform a health check process for determining whether a set of showing contacts should be allowed to proceed with said selected showing appointment, wherein said health check process comprising:
(a) configuring said remote electronic communication device to determine a set of values of a health parameter for said set of showing contacts respectively;
(b) retrieving said set of values from said remote electronic communication device; and
(c) determining whether said set of values matches a set of health thresholds by itself or by relying on said specialized server software application;
9) when said set of values matches said set of health thresholds, retrieve a showing directive for said selected showing appointment from said specialized server software application;
10) present showing directive via said remote electronic communication device, wherein said showing directive is:
(a) displayed on said display screen of said remote electronic communication device; or
(b) presented in an audio format; and
11) wherein:
i) said health parameter is a human body temperature parameter;
ii) said set of health thresholds includes a normal body temperature limit; and
iii) said specialized remote software application presents a prompt to each respective showing contact in the set of showing contacts to take a temperature reading using an infrared thermometer that is either incorporated in the remote electronic communication device or is activated and/or accessed by the specialized remote software application via an application programming interface call, and receives the results of said temperature readings.

2. The real estate showing appointment management system of claim 1 wherein,
i) said set of values matches a set of health thresholds when each value within said set of values is below said normal body temperature limit; and
ii) said set of values does not match said set of health thresholds when any value within said set of values is above said normal body temperature limit.

3. The real estate showing appointment management system of claim 1 wherein said showing directive includes at least one of a showing pass or a key code corresponding to said selected showing appointment.

4. The real estate showing appointment management system of claim 3 wherein said showing directive further includes a set of showing instructions.

5. The real estate showing appointment management system of claim 1 wherein said health check process further comprises:
i) presenting a set of health inquiries via said remote electronic communication device;
ii) retrieving a set of responses to said set of health inquiries via said remote electronic communication device; and
iii) determining whether said set of responses meets a set of health requirements by itself or relying on said specialized server software application.

6. The real estate showing appointment management system of claim 5 wherein said set of values is said to match a set of health thresholds when each value within said set of values is below said normal body temperature limit, and said set of values is said to not match said set of health thresholds when any value within said set of values is above said normal body temperature limit.

7. The real estate showing appointment management system of claim 6 wherein said showing directive includes at least one of a showing pass or a key code corresponding to said selected showing appointment.

8. The real estate showing appointment management system of claim 7 wherein said showing directive further includes a set of showing instructions.

9. A method for managing showing appointment based on a set of health parameters, said method performed by a real estate showing appointment management system and comprising:
1) receiving a request for making a showing appointment of a listing;
2) creating said appointment;
3) requesting a listing contact of said listing to confirm said showing appointment;
4) receiving a confirmation of said showing appointment;
5) indicating said showing appointment as confirmed;
6) presenting said showing appointment on a display screen of a remote electronic communication device;
7) determining a first geographical location of said listing;
8) determining a second geographical location of said remote electronic communication device;
9) determining whether said remote electronic communication device is within a geofence of said listing based on said geofence, said first geographical location and said second geographical location;

10) when said remote electronic communication device has moved into said geofence, performing a health check process to determine whether a set of showing contacts should be allowed to proceed with said showing appointment, wherein said health check process comprising:
  (a) configuring said remote electronic communication device to determine a set of values of a health parameter for said set of showing contacts respectively;
  (b) retrieving said set of values from said remote electronic communication device; and
  (c) determining whether said set of values matches a set of health thresholds;

11) when said set of values matches said set of health thresholds, presenting a showing directive via said remote electronic communication device, wherein said showing directive is:
  (a) displayed on said display screen of said remote electronic communication device; or
  (b) presented in an audio format; and 12) wherein:
  i) said health parameter is a human body temperature parameter;
  ii) said set of health thresholds includes a normal body temperature limit; and
  iii) said real estate showing appointment management system presents a prompt to each respective showing contact in the set of showing contacts to take a temperature reading using an infrared thermometer that is either incorporated in the remote electronic communication device or is activated and/or accessed by said real estate showing appointment management system via an application programming interface call, and receives the results of said temperature readings.

10. The method of claim 9 wherein:
  i) said set of values matches a set of health thresholds when each value within said set of values is below said normal body temperature limit; and
  ii) said set of values does not match said set of health thresholds when any value within said set of values is above said normal body temperature limit.

11. The method of claim 9 wherein said showing directive includes at least one of a showing pass or a key code corresponding to said selected showing appointment.

12. The method of claim 11 wherein said showing directive further includes a set of showing instructions.

13. The method of claim 9 wherein said health check process further comprises:
  i) presenting a set of health inquiries via said remote electronic communication device;
  ii) retrieving a set of responses to said set of health inquiries via said remote electronic communication device; and
  iii) determining whether said set of responses meets a set of health requirements.

14. The method of claim 13 wherein said health check process is said to have passed successfully when each value within said set of values is below said normal body temperature limit, and said health check process is said to have not passed successfully when any value within said set of values is above said normal body temperature limit.

15. The method of claim 14 wherein said showing directive includes at least one of a showing pass or a key code corresponding to said selected showing appointment.

16. The method of claim 15 wherein said showing directive further includes a set of showing instructions.

* * * * *